United States Patent [19]

Perna

[11] Patent Number: 4,576,216

[45] Date of Patent: Mar. 18, 1986

[54] PROCESS FOR MANUFACTURING INVESTMENT MOLDS

[75] Inventor: Giorgino Perna, Turin, Italy

[73] Assignee: Newellpharma s.r.l., Turin, Italy

[21] Appl. No.: 669,295

[22] Filed: Nov. 8, 1984

[30] Foreign Application Priority Data

Nov. 8, 1983 [IT] Italy ............................... 68159 A/83

[51] Int. Cl.$^4$ ........................... B22C 15/20; B28B 7/36
[52] U.S. Cl. ...................................... 164/21; 106/38.2; 106/38.22; 106/38.25; 106/38.3; 164/15; 164/37; 164/44; 164/376
[58] Field of Search ................. 106/38.25, 38.3; 164/6, 164/13, 15, 21, 37, 44, 376

[56] References Cited

U.S. PATENT DOCUMENTS 2,720,687 10/1955 Shaw ..................................... 164/21
2,770,859 11/1956 Henry ................................... 164/44

Primary Examiner—Lorenzo B. Hayes
Attorney, Agent, or Firm—Sughrue, Mion, Zinn, Macpeak, and Seas

[57] ABSTRACT

A process for making an investment mold wherein a paste composition is used as the separating layer between the investment mould of refractory material and the surface of the metal container in which the investment mould itself is located. The composition is constituted by an organic component which can be eliminated by thermal degradation at temperatures above 200° C. and a refractory mineral component which is stable at the casting temperature of the alloy used in the casting process. In a preferred embodiment, the composition comprises vaseline, talc and kaolin.

6 Claims, No Drawings

PROCESS FOR MANUFACTURING INVESTMENT MOLDS

The present invention relates to a composition in paste-form for use in lost-wax casting processes as the layer separating the investment mould of refractory material from the inner surface of the metal container in which the investment mould is located. The composition is useful particularly in lost-wax, precision-casting processes used in dental technology.

It is known that, in lost-wax casting processes, an investment mould constituted by refractory material and binders is used. The refractory material expands during the setting and heating process preceeding the casting and this expansion must be taken into account in order to compensate for dimensional variations of the alloy used for the casting during its cooling and solidification. The corrective factor to be taken into account is determined by the properties of the refractory material and the technique used for the preparation of the model. The possibility of obtaining a casting with the desired dimensional precision necessary for example in dental technology depends on the refractory material being free to behave in a reproducible manner according to its own intrinsic properties. Any constraint which opposes the natural expansion of the investment mould can have a harmful effect on the final result, with the possibility of fracture of the model or lack of the required precision in the casting.

In dental technology it is common practice to place strips of asbestos soaked in water between the container, which is generally a hollow metal cylinder, and the investment mould itself. The strips of asbestos allow partial expansion of the refractory material and also separate the refractory investment mould from the inner surface of the metal cylinder during the high temperature treatment in the furnace. The use of asbestos for the separating and coating material is however satisfactory, particularly when the investment mould is constituted by a refractory material including phosphates which is used in processes for casting alloys with high solidification temperatures. In fact, in such cases, the asbestos layer adheres to the investment mould at the casting temperature to such an extent that it is rather difficult and laborious to remove the investment itself after the casting has cooled. The use of asbestos is also undesirable from a health point of view.

In order to avoid the disadvantages mentioned above, the present invention provides a composition in paste-form for use in lost-wax casting processes as the layer for separating the investment mould of refractory material from the surface of the metal container, characterised in that it is constituted by:

(A) an organic component which can be eliminated by thermal degradation at a temperature above 200° C., and (B) a powdered, refractory-mineral component which is stable at the casting temperature of the alloy used in the casting process.

The organic component used for the composition according to the invention must have a chemical composition such as not to give rise to toxic gases as a result of its thermal decomposition.

The organic component is preferably selected from the group of waxes and paraffin waxes having dropping points below 60° C. and preferably is present in quantities of from 30 to 60% by weight with respect to the weight of the composition.

Preferably micro-crystalline paraffin waxes or petrolata, particularly vaseline, ozocerite and ceresine are used.

The refractory mineral component is preferably a mixture comprising:

(a) a component selected from the group consisting of talc, mica, titanium dioxide and mixtures thereof, and (b) a component selected from the group of kaolin, diatomite, bentonite and mixtures thereof; the weight ratio of the component (a) to the component (b) preferably being 1.2 to 3.

Preferably the total quantity of the component B is from 70 to 40% by weight with respect to the weight of the composition.

Preferably the component (a) and the component (b) are in granular form with dimensions of less than 60 microns, that is, such as not to leave a residue on a sieve of the SB no. 300 series.

In a preferred embodiment, the composition is made up of from 52 to 60% by weight of vaseline with reference to the weight of the composition and from 48 to 40% by weight, with respect to the weight of the composition of a refractory mineral mixture comprising (a) talc and (b) kaolin, the ratio by weight of the talc to the kaolin being from 2 to 2.5.

The components of the composition which is the subject of the present invention must have a purity up to pharmacopoeial standards.

The preparation of the composition does not present any particular problems. It in fact suffices to heat the organic component, normally a semi-solid at ambient temperatures, to a temperature generally between 40° and 60° C. at which the organic component appears to be a viscous liquid and then to add the previously-prepared, powdered refractory mixture in small portions and with agitation.

The prepared composition is in the form of a thixotropic paste.

A second subject of the invention is a lost-wax casting process which includes the step of applying a layer of the paste composition having the characteristics specified above to the inner surface of the metal container which will receive the investment mould of refractory material.

The application is carried out under cold conditions, a thin layer of the composition being applied with a spatula or with simple finger pressure. For example, for a hollow container having an internal diameter of 70 mm it suffices to apply a layer of the composition with a thickness of the order of about 1 mm. For a hollow cylinder having an internal diameter of 100 mm a layer with a thickness of the order of 1.5 to 1.8 mm may suffice.

Th rheological characteristics of the composition are such that it is not necessary to apply a layer of rigorously-uniform thickness, compensation for the thickness being allowed during the expansion of the refractory material in the setting and hardening stage. The characteristics of the composition are also such as to allow the refractory material to expand by about 50 to 60% with reference to the thickness of the layer without any appreciable mechanical resistance even when cold.

As a result of the treatment in the furnace, the organic component of the composition in question is eliminated by thermal degradation at temperatures above 200° C.

leaving an inert residue. The expansion allowed during the heating phase at temperatures above 200° C. is of the order of 90 to 97% of the original thickness of the layer.

After treatment in the furnace and after casting, the layer of the composition is still compressible by slight mechanical action without the use of special instruments and allows the refractory investment to be removed easily from the metal container.

EXAMPLE 1

A paste having the following percentage by weight composition is prepared:

F.U. vaseline: 57%
B.P. talc, French code F.U. PH USP: 29%
Washed kaolin (clay) (Carlo Erba): 14%

The composition is left to cool and to rest for 24 hours and is then used in a lost-wax casting process for the precision casting of a gold alloy with a high fusion point. An investment mould is used which is made from a phosphate-based refractory material, having the form of a cylinder with an outer diameter of about 68 mm. The composition is spread, while cold, with the aid of a spatula in a thin layer having a thickness of about 1 mm on the inner surface of the container constituted by a hollow metal cylinder having an internal diameter of 70 mm. The investment mould is then introduced into the hollow metal cylinder and left there for a setting time of at least one hour. The cylinder and its investment mould are then placed in a furnace previously heated to a temperature of 350° C. and kept at this temperature for at least 30 minutes. Subsequently the temperature of the furnace is raised to 700° C. and this temperature is maintained for at least 45 minutes. The casting is then carried out by the centrifugal technique, the alloy being melted in a refractory crucible with the use of a propane-oxygen torch.

After cooling, the investment mould of refractory material may easily be extracted from the metal container and the thin residual layer of the composition may be removed easily. The casting has the required precision.

EXAMPLE 2

The process of Example 1 is repeated with the use of the same paste composition but with a gypsum-based refractory material. The maximum temperature of the furnace, at which the investment is kept for 45 minutes, is in this case 650° C.

Again in this case the investment mould of refractory material may be extracted easily from the metal container and the thin residual layer may be removed easily; the casting has the required precision.

What is claimed is:

1. In a process for manufacturing an investment mold of refractory material for casting metal alloys comprising applying a layer of a paste composition to the inner surface of a metal container prior to forming the mold therein, wherein said layer is suitable for separating said mold from said container; the improvement comprising, as said paste composition,
    (A) an organic component which can be eliminated by thermal degradation at a temperature above 200° C., and
    (B) a powdered, refractory-mineral component which is stable at the casting temperature of said alloy used in said casting process.

2. A process as claimed in claim 1, wherein said organic component is selected from the group of waxes having dropping points below 60° C. and comprises from thirty to sixty percent by weight of the weight of said composition.

3. A process as claimed in claim 2, wherein said organic component is selected from the group consisting of petrolatum, ozocerite and ceresine.

4. A process as claimed in claim 1, wherein said powdered refractory-mineral component comprises from forty to seventy percent by weight of the weight of said composition and consists of a mixture comprising:
    (a) a material selected from the group consisting of talc, mica, titanium dioxide and mixtures thereof, and
    (b) a material selected from the group of kaolin, diatomite, bentonite and mixtures thereof; the ratio by weight of said constituent (a) to said constituent (b) being from 1.2 to 3.

5. A process as claimed in claim 1, wherein said organic component is petrolatum which comprises from fifty-two to sixty percent by weight of the weight of said composition, and said powdered refractory mineral component comprises from forty to forty-eight percent by weight of the weight of said composition and comprises talc and kaolin in a ratio by weight of from 2 to 2.5.

6. A process as claimed in claim 1, wherein said powdered refractory-mineral component is in the form of granules having dimensions of less than 60 microns.

* * * * *